US00PP24630P2

(12) United States Plant Patent
Blom

(10) Patent No.: US PP24,630 P2
(45) Date of Patent: Jul. 8, 2014

(54) ***ECHINACEA* PLANT NAMED 'HONEYDEW'**

(50) Latin Name: ***Echinacea* hybrid**
Varietal Denomination: Honeydew

(76) Inventor: Arie Blom, Oudewater (NL)

( * ) Notice: Subject to any disclaimer, the term of this patent is extended or adjusted under 35 U.S.C. 154(b) by 175 days.

(21) Appl. No.: 13/507,850

(22) Filed: Aug. 1, 2012

(51) Int. Cl.
*A01H 5/00* (2006.01)

(52) U.S. Cl.
USPC ..... Plt./428

(58) Field of Classification Search
CPC ..... A01H 5/025
USPC ..... Plt./428
See application file for complete search history.

*Primary Examiner* — June Hwu
(74) *Attorney, Agent, or Firm* — Penny J. Aguirre

(57) ABSTRACT

A new cultivar of hybrid *Echinacea*, 'Honeydew', characterized by its large anemone-type composite flowers with ray florets that are greenish white in color and disc florets that are light green in color, its strong stems, its short plant height, and its compact plant habit.

2 Drawing Sheets

Botanical classification: *Echinacea* hybrid.
Variety denomination: 'Honeydew'.

BACKGROUND OF THE INVENTION

The present invention relates to a new and distinct cultivar of *Echinacea* of hybrid origin and will be referred to hereafter by its cultivar name, 'Honeydew'. 'Honeydew' represents a new coneflower, an herbaceous perennial grown for landscape use.

The new cultivar arose from an ongoing breeding program of the Inventor's in Zuidwolde, The Netherlands. The objective of the breeding program is to develop new cultivars of anemone type *Echinacea* with horizontal ray florets in unique and strong colors. The new cultivar arose from open pollination of an unnamed plant from the Inventor's breeding, designated as Ec 7073-08, in summer of 2008. The male parent is unknown. 'Honeydew' was selected as single unique plant from the resulting seedlings in September of 2009.

Asexual reproduction of the new cultivar was first accomplished by in vitro propagation in Heerhugowaard, The Netherlands in November of 2009 under the direction of the Inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Honeydew' as a unique cultivar of *Echinacea*.

1. 'Honeydew' exhibits large anemone-type composite flowers.
2. 'Honeydew' exhibits inflorescences with ray florets that are greenish white in color and disk florets that are light green in color.
3. 'Honeydew' exhibits ray florets that are long and held horizontal.
4. 'Honeydew' is short in height and exhibits a compact plant habit.
5. 'Honeydew' exhibits strong stems.

The female parent, designated as Ec 7073-08, differs from 'Honeydew' in having a cone area that is smaller in diameter, in having disk and rays florets that are pink in color, and in being taller in height with weaker stems. The new cultivar can be most closely compared to the cultivars 'Meringue' (U.S. Plant Pat. No. 20,537) and 'Coconut Lime' (U.S. Plant Pat. No. 18,617). 'Meringue' differs from 'Honeydew' in having inflorescences that are less green in color, in having spines on the disk florets of young inflorescences that are visible (not visible on 'Honeydew'), and in being shorter in height. 'Coconut Lime' differs from 'Honeydew' in having smaller inflorescences, ray florets that are held more downward, in having spines on the disk florets of young inflorescences that are visible resulting in a yellow coloration to the disk florets, and in being taller in height.

BRIEF DESCRIPTION OF THE DRAWING

The plants in the accompanying photographs depict the characteristics of a one year-old plant of 'Honeydew' as field grown in Zuidwolde, The Netherlands. Stems were cut at ground level and placed in a vase for the photographs.

The photograph in FIG. 1 shows a group of cut stems.

Figure 1:
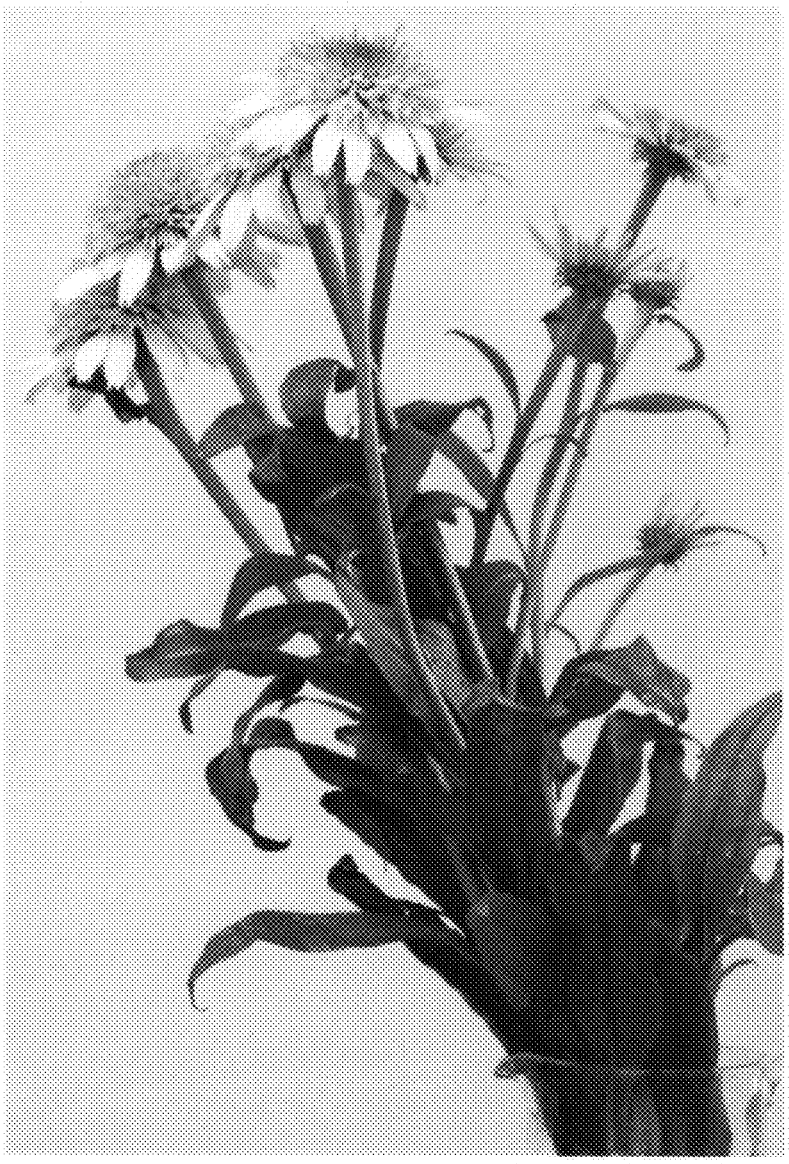
Figure 2:
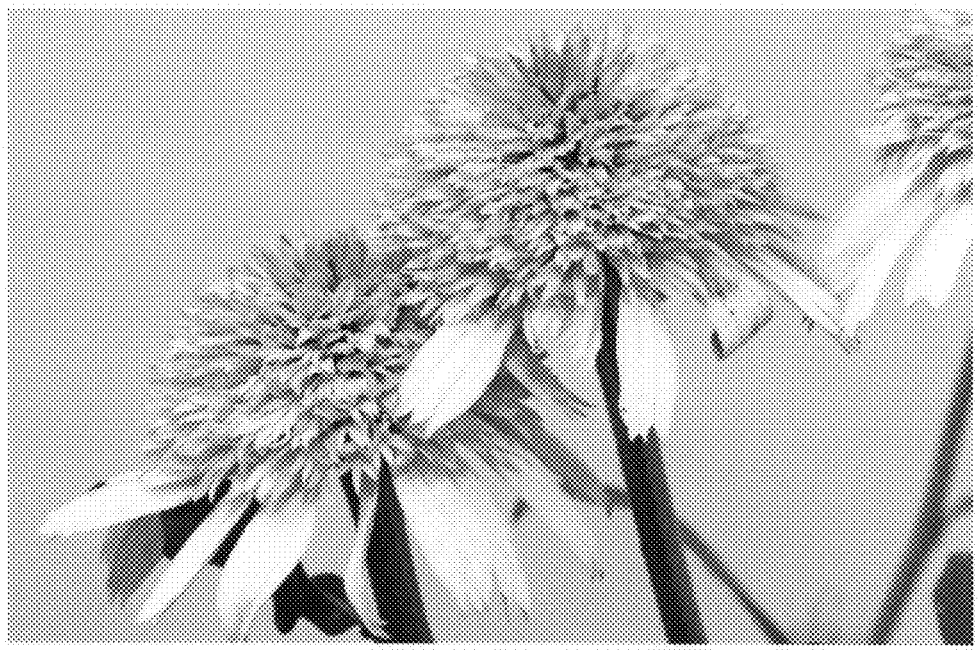

The photograph in FIG. 2 provides a close-up view of inflorescences of 'Honeydew'.

Figure 3:
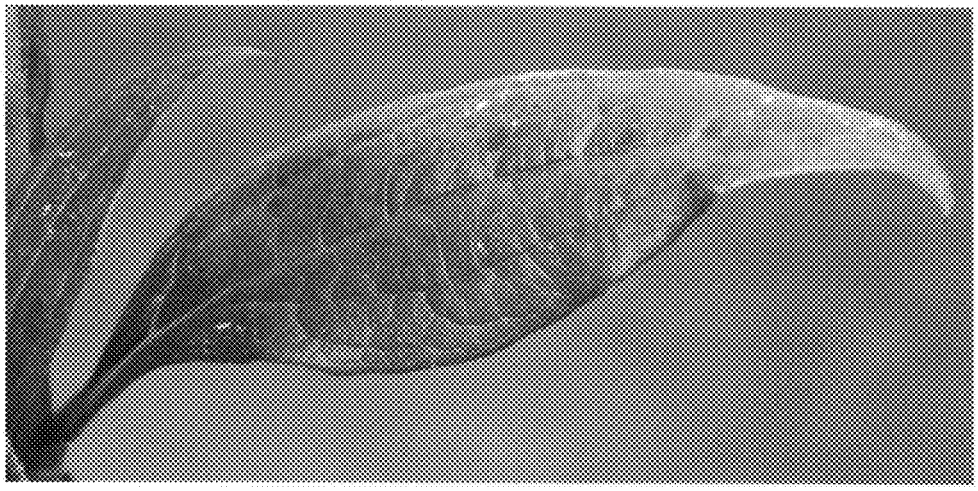

The photograph in FIG. 3 provides a close-up view of a leaf of 'Honeydew'. The colors in the photograph may differ slightly from the color values cited in the detailed botanical description, which accurately describe the colors of the new *Echinacea*.

BOTANICAL DESCRIPTION OF THE PLANT

The following is a detailed description of one year-old plants of the new cultivar as field grown in Zuidwolde, The Netherlands. Plants were grown under average day temperatures ranging from 12° to 28° C. and average night temperatures of 6° to 16° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Continuously from end of June through August in The Netherlands.

*Plant habit*.—Herbaceous perennial, clump forming, upright and strong stems, compact.

*Height and spread*.—About 55.6 cm in height and 38.2 cm in spread.

*Cold hardiness*.—At least to U.S.D.A. Zones 3 and 4.

*Diseases and pests*.—No particular resistance or susceptibility to pests or diseases has been observed.

*Root description*.—Fibrous.

Growth and propagation:

*Propagation*.—Tissue culture preferred.

*Growth rate*.—Moderately vigorous.

Stem description:

*Shape*.—Rounded.

*Stem color*.—Between 144D and N144D, lenticels 147B to 147C.

*Stem size*.—Average of 6 mm in diameter and an average of 41.2 cm in height.

*Stem surface*.—Moderately covered with short strigose hairs; 0.5 mm in length, NN155C to NN155D in color.

*Stem strength*.—Very strong.

*Stem aspect*.—Stems grow in an average angle of 25° from the base (0°=vertical).

*Stem number*.—Average of 5 main stems.

*Branching*.—2 lateral branches per main stem.

Foliage description:

*Leaf shape*.—Ovate to narrowly elliptic.

*Leaf division*.—Simple.

*Leaf base*.—Long attenuate to narrow cuneate.

*Leaf apex*.—Acute.

*Leaf venation*.—Pinnate, upper surface; 143B, lower surface; 143C.

*Leaf margins*.—Entire, slightly undulate.

*Leaf attachment*.—Petiolate.

*Leaf arrangement*.—Alternate.

*Internode length*.—An average of 7.7 cm.

*Leaf size*.—Average of 14 cm in length and 4.2 cm in width.

*Leaf color*.—Young upper surface; 137A, young lower surface; 138A, mature upper surface; N137A, mature lower surface; 147B.

*Leaf surface*.—Upper surface is moderately glossy, lower surface is slightly glossy, both surfaces moderately covered with very short strigose hairs; average length of 0.3 mm and 157D in color.

*Petioles*.—Upper stem leaves nearly sessile, average length of petioled leaves is 5.2 cm in length, v-shaped petiole is 3 mm in height and 2 mm in width, upper and lower surfaces smooth, moderately covered with very short strigose hairs 0.3 mm in length and 157D in color, upper surface color; 144B, margins N137A to N137B, lower surface color; 144A to 144B, margins N137A to N137B.

Flower description:

*Type*.—Terminal capitulum, heterogamous with ray florets around the head margin and anemone-type disc florets in the center.

*Capitulum number*.—One terminal capitulum per main stem and lateral branch.

*Lastingness of inflorescence*.—About 10 days.

*Capitulum size*.—Matures to about 5.4 cm in height and 8.7 cm in diameter, disk size is 6.5 cm in diameter.

*Fragrance*.—None.

*Involucral bracts or phyllary*.—About 48 arranged in 3 overlapping rows, up to 1 cm in length and 4 mm in width, dull in appearance, cuneate at base, acute apex, ovate in shape, entire margins moderately covered with short hairs 0.3 mm in length and NN155C to NN155D in color, upper surface; smooth and 137A in color, lighter base 143C in color, lower surface smooth and 137A in color, lighter base 143C in color and moderately covered with short hairs 0.3 mm in length and NN155C to NN155D in color.

*Buds*.—Flattened globular in shape with immature ray florets pointed upright, up to 2.9 cm in diameter and 2.6 cm in length, between N137A and 147A, immature ray florets 150B.

*Peduncle*.—Strong, straight on top of main (flowering) stem, average angle of secondary and tertiary peduncles 25° (0°=straight upright), terminal peduncle length is 10.5, diameter of peduncle is 7 mm, between 144D and N144D, tip 147B to 147C in color, surface is covered with short strigose hairs, 1 mm in length and NN155C to NN155D in color.

*Ray florets*.—Rotate, about 17, oblanceolate in shape, about 4.3 cm in length and 1.2 cm in width, praemorse apex, cuneate base, entire margin, moderately drooping in an average angle of −40°, upper and lower surface texture is smooth and ribbed lengthways (carinate), color: when opening upper surface; 8A, base 7D, when opening lower surface; 1C, when fully opened upper surface; between 145D and 150D, when fully opened lower surface; 145B to 145C.

*Disc florets* (*bisexual*).—Numerous, about 350, narrowly oblong in shape, 80% of all petals are fused, arranged spirally on disc, about 2 cm in length and 2.5 mm in width, entire margin, upper surface smooth, dull and slightly velvety in appearance, lower surface smooth and slightly glossy in appearance, color: upper surface when opening; 3C, tip 145A, lower surface when opening; 150B, tip 145A, upper and lower surfaces when fully opened; 145C, base 145B.

*Receptacle*.—Triangular in shape, about 1.2 cm in diameter and 1.4 cm in height, color NN155B, base 157A.

*Receptacle spines*.—Average of 350, acicular in shape, acute apex, attenuate base, smooth and glossy surface, color: apex; 13B, mid-section; 144A, base; 144B.

Reproductive organs:

*Gynoecium*.—Pistil; 1 (only present in disc florets), 8 mm in length, style; 6 mm in length and 157D in color, ovary; 157D in color.

*Androcoecium*.—Stamens; 4 (only present in disc florets), filament 2 mm in length and 145D in color, anther; narrow oblong in shape, 1 mm in length and N199D in color, no pollen detected.

*Fruit/seed*.—No fruit or seed detected to date.

It is claimed:

1. A new and distinct cultivar of *Echinacea* plant named 'Honeydew' substantially as herein illustrated and described.

* * * * *